United States Patent [19]

Kamen

[11] Patent Number: 4,645,175

[45] Date of Patent: Feb. 24, 1987

[54] MODULAR CLAMP SYSTEM WITH EXTERNALLY THREADED ADJUSTER

[75] Inventor: Dean L. Kamen, Bedford, N.H.

[73] Assignee: Baxter Travenol Laboratories, Deerfield, Ill.

[21] Appl. No.: 551,956

[22] Filed: Nov. 15, 1983

Related U.S. Application Data

[63] Continuation-in-part of Ser. No. 479,328, Mar. 28, 1983, which is a continuation-in-part of Ser. No. 336,068, Dec. 31, 1981, Pat. No. 4,410,164.

[51] Int. Cl.$^4$ .............................................. F16L 55/14
[52] U.S. Cl. ........................................ 251/9; 604/250
[58] Field of Search ..................... 251/4–10; 604/250; 24/135 R, 278

[56] References Cited

U.S. PATENT DOCUMENTS

| | | | |
|---|---|---|---|
| 2,915,078 | 12/1959 | Ochs, Jr. ................................. | 251/5 |
| 2,935,088 | 5/1960 | Thompson et al. ..................... | 251/8 |
| 3,167,299 | 1/1965 | Ling ........................................ | 251/8 |
| 3,915,167 | 10/1975 | Waterman ............................... | 251/9 |
| 4,312,493 | 1/1982 | Stauffer .................................. | 251/8 |
| 4,355,783 | 10/1982 | Morin .................................... | 251/9 |
| 4,410,164 | 10/1983 | Kamen .................................... | 251/9 |

Primary Examiner—James C. Yeung
Attorney, Agent, or Firm—Bromberg, Sunstein & McGregor

[57] ABSTRACT

A modular clamp system in one embodiment has a case having an inlet and an outlet port, forming a housing for a resilient flow tube. Attached to the housing is a clamping member having two arms between which the flow tube passes. One end of the pair of arms fits within and is engaged by the hollow bore of threaded adjuster which is guided by the case. Turning the adjuster advances it, causing the arms to be pushed closer together, so as to progressively constrict the flow tube at a controllable rate. The arms may be tapered and the bore a right cylindrical bore, or the bore may be tapered and the arms untapered, in which case the tips of the arms contact with the interior face of the bore. The fineness of the screw threads and the degree of taper of the adjuster contacting surfaces may be so chosen that a full rotation of the adjuster causes a very small adjustment in flow rate. In one embodiment, the arms contain a transverse portion forming a collet surrounding the flow tube and cemented to it for positively deconstricting the flow tube upon release or opening of the valve. In another embodiment, the clamp forms an assembly which can be attached to an auxiliary control mechanism further embodiment, the adjuster has an integrally formed toothed gear, to permit uniform incremental rotation by the auxiliary control system.

32 Claims, 7 Drawing Figures

MODULAR CLAMP SYSTEM WITH EXTERNALLY THREADED ADJUSTER

This application is continuation-in-part of my copending application Ser. No. 479,328, filed Mar. 28, 1983, which was a continuation-in-part of my application Ser. No. 336,068, filed Dec. 31, 1981, now U.S. Pat. No. 4,410,164, all of which are incorporated herein by reference.

TECHNICAL FIELD

This invention relates to clamps for controlling the rate of flow of a medical infusion through a tube by constriction of the tube's exterior, and to such clamps for use with automatic flow rate sensing and controlling means.

BACKGROUND OF THE INVENTION

A broad variety of medical infusion clamps are known in the prior art. Typically such clamps operate by clamping down on the exterior surface of an infusion tube, thereby partially constricting the flow path. Such devices are generally used in conjunction with a drip chamber, allowing visual monitoring of the actual rate of flow. Prior art devices of this general type are disclosed in U.S. Pat. Nos. 2,908,476 and 3,960,149. While such a clamp has the advantage of low cost and simplicity of operation, the use of a tube clamp to regulate flow is complicated by the fact that constriction of a tube results in cold flow of the displaced tube wall and consequent changes in the flow path shape and thus in the flow rate over the minutes or hours following clamp adjustment. In use, hospital personnel must therefore periodically monitor such flow clamps and re-set the clamp to account for the flow rate "drift." Such drift may amount to as much as 50% of the selected flow rate over an interval of 20 minutes or less. An additional limitation of such clamps is that tubing, once clamped, does not assume its original shape upon release. This lack of "memory" has as a consequence that when a tube is initially overclamped one cannot simply release the clamp and reset it to a proper value. Instead irregular flow rates will persist for some time as the tubing slowly deconstricts toward its initial shape. Each of these factors requires frequent monitoring and adjustment to attain an acceptable degree of precision in flow rate, thus placing demands upon hospital personnel. These demands can be reduced by using an automated flow adjusting device, such as the device of U.S. Pat. No. 4,137,940; however such a device is significantly more expensive than a simple plastic flow clamp. A problem thus exists as to how to construct a simple flow clamp capable of being manually set to a stable flow rate and requiring minimal human monitoring. A problem also exists as to how to construct such a flow clamp adaptable to, but not requiring, automatic control means and having the structural simplicity and ease of operation of a conventional manually operated valve. A further problem exists as to the design of such a clamp capable of stable control over a broad range of desired flow rates without such range or stability being impaired by variations the clamp elements within normal manufacturing tolerances.

BRIEF DESCRIPTION OF THE INVENTION

The present invention overcomes the foregoing problems by providing in one embodiment a case having an inlet and an outlet port, forming a housing for a resilient flow tube. Attached to the housing is a clamping member having two arms between which the flow tube passes. One end of the pair of arms fits within and is engaged by the hollow bore of an externally threaded adjuster which screws into the case. Turning the adjuster advances it, causing the arms to be pushed closer together, so as to progressively constrict the flow tube at a controllable rate. The arms may be tapered and the bore a right cylindrical bore, or the bore may be tapered and the arms untapered, in which case the tips of the arms contact with the interior face of the bore. The fineness of the screw threads and the degree of taper of the adjuster contacting surfaces may be so chosen that a full rotation of the adjuster causes a very small adjustment in flow rate. In one embodiment, the arms contain a transverse portion forming a collet surrounding the flow tube and cemented to it for positively deconstricting the flow tube upon release or opening of the valve. In another embodiment, the clamp forms an assembly which can be attached to an auxiliary control mechanism without interupting or altering the flow setting. In a further embodiment, the adjuster has an integrally formed toothed gear, to permit uniform incremental rotation by the auxiliary control system. These and other features of the invention will become apparent by reference to the drawings.

DETAILED DESCRIPTION OF THE INVENTION

Figure 1:
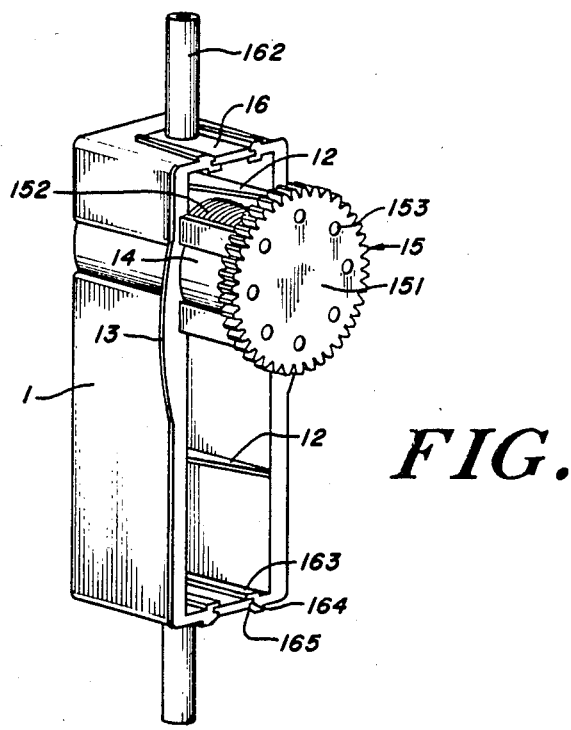
FIG. 1 shows an embodiment of a modular clamp according to the present invention.

FIG. 1 shows one embodiment of a modular clamp according to the present invention, with attached inlet tube 162 and corresponding outlet tube (not numbered), both of conventional type. The clamp includes a case 1 through which passes a flow tube, discussed below in connection with FIG. 5. The inlet tube 162 connects to the case at a nipple plate 16 at one end of the case. The outlet tube connects to a corresponding element at the opposite end of the case. Between the two passes a flow tube connected to corresponding nipples on the inner sides of nipple plates 16. In the embodiment shown, the case is molded of a relatively thin plastic and the case acquires structural strength from the box-like configuration, as well as from a number of ribs 12 spaced along its length. The nipple plates, which contribute to the ease of installation of the flow tube, snap into position in grooves 164 formed between abutment rails 163 and the raised border 165 located on the inner and outer faces respectively of an aperture in the casing at each end. Situated to effect the clamping action on the flow tube within the case is an adjuster 15 which screws into the case at a bore defined by opposing extensions 14 of opposite sidewalls of the case. Also shown in FIG. 1 is mounting flange 13 laterally projecting from the casing, the function of which will be more fully explained in connection with FIG. 7 below. A plurality of apertures 153 in the adjuster 15 are also shown, as more fully explained below in connection with FIG. 2.

Figure 2:
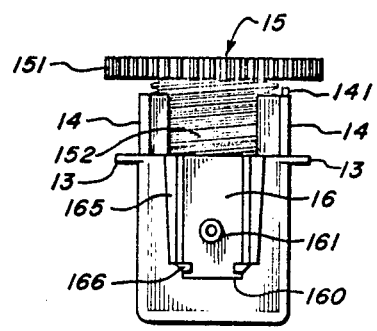
FIG. 2 is an end view of the clamp of FIG. 1.

Turning now to FIG. 2, there is shown an end view of the clamp case, without the inlet tube. The adjuster 15 has an upper portion 151 in the form of a toothed gear and a lower portion 152 that is externally threaded. Turning of the toothed gear 151 advances or retracts the adjuster within a bore defined by arcuate segments consisting of extensions 14 of opposing sidewalls of the case. These extensions each comprise substantially less than a semicircle of arc and are not connected to each other across the middle, so that the bore formed thereby has a substantial degree of flexibility. The extensions 14 define cylindrical segments, or guides, internally threaded so as to mate with the threaded adjuster portion 152, and of sufficient size to dependably engage the adjuster. Rising from one extension 14 is a limit lock pin 141. This pin, which may be formed as an integrally molded projection from the case, is positioned to engage the apertures 153 as the adjuster is rotated into the guide bore. The adjuster is configured to operate with a co-acting clamp member, discussed below, within the case in such manner as to progressively constrict the flow tube as the adjuster is advanced into the case. As the adjuster nears the limit of its advance, the pin 141 operates to make a noise accompanied by rough and irregular impacts which may be felt by an attendent turning the adjuster, so that the attendant will be aware that the clamp has reached its limits of operation. The pin also serves to lock the adjuster in the extreme position after use to discourage reuse or continued use of a clamp which has been abused by overadjustment.

Below the extensions 14 in FIG. 2 are shown the mounting flanges 13, of substantially uniform thickness, laterally projecting from the case so as to define a plane. At the inlet end of the case is inlet nipple 161, in the nipple plate 16, to which the inlet tube attaches. The nipple plate 16 is preferably integrally formed with the case 1 and is attached thereto along a hinge line 160, discussed below with reference to FIG. 4, via a thin and flexible portion of the case surface. In operative position, the hinge plate occupies a U- shaped aperture in the end wall of the case, and is retained in position by a pair of laterally extending wings 168, also shown in FIG. 4, which snap-fit into the groove 164 defined by raised border 165 on each edge of the aperture. As may be seen, the raised border extends from the plane defined by the mounting flanges 13 down to a point somewhat above the hinge line 160. A pair of laterally protruding raised dogs 166 on the nipple plate 16 assure that should the nipple plate become disconnected from the case, it cannot slide up past the raised border 165. In this manner the nipple plate to which various flow tubes attach remains in a position centered along a major axis of the case.

Figure 3:
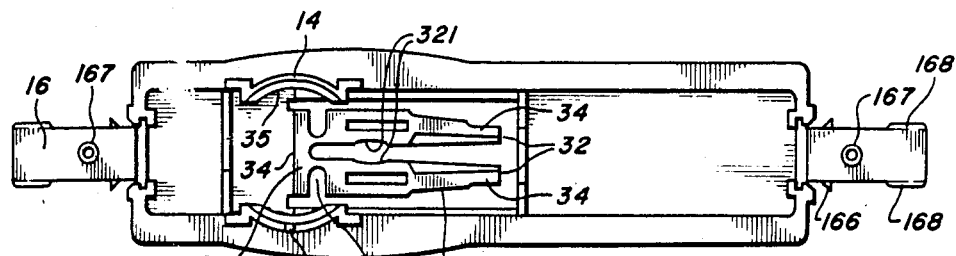
FIG. 3 is a top view of the same embodiment, without adjuster, before assembly.

In FIG. 3, there is shown a top view of the case. Nipple plates 16 are shown extending outwardly from the case, at either end thereof. Also visable is inner nipple 167 in each nipple plate, to which a medicinal flow tube, discussed below in connection with FIG. 5, will be attached. Aligned between the two nipple plates is fork 31, also formed integrally with the case and connected thereto at a hinge line 34 at the base of the fork. As may be seen, hinge line 34 is directly below the projection of a diameter of the circular guide bore defined by extensions 14. In this manner the fork 31 may be folded upward along its hinge so as to be centered within the bore. The fork 31 comprises a pair of arms 32, of which the lower end is held in fixed spaced part relation by the body of the fork and the upper end is free. The two arms 32 define a gap therebetween. Opposing contact faces 321 on the inner side of each arm are situated so as to surround the line determined by inlet and outlet inner nipples 167 when the nipple plates 16 are folded up into operative position and the fork is rotated upward. On the side of each arm 32 opposing the tube contact faces 321 and near to the free end thereof is a contoured portion 322. The contour of this portion is symmetric, on each arm, with respect to a central axis and is configured to engage an interior face of adjuster 15, which has a hollow bore therein, and to be laterally moved thereby as the adjuster advances. Thus, for a tapered bore in the adjuster 15, the arms may have a simple rounded tip. In the embodiment shown, the contacting face 322 of each arm is tapered at a uniform taper so as to be pressed inwardly when the adjuster advances. Also shown is a narrowed portion 34 at the very tip of each fork which, through a contour, leads to a wider tapered contacting face 322. The narrowed portion facilitates initial insertion of the arms into the adjuster. In use, turning of the adjuster advances it down along the contacting faces 322, forcing the two arms together to squeeze the flow tube passing therebetween via the tube contacting faces 321. The fork is formed with a flex relief cutaway 33 below each arm between the arm and the base of the fork. This results in the remaining narrow portion of the fork acting as a hinge along an axis parallel to the flow tube, so that the arms 32 are subject to lateral displacement by the adjuster 15 with a minimal amount of force required. In effect, the arms have a parallel pair of mildly elastic hinges at their base. This parallel hinge arrangement makes the clamping action of the arms relatively insensitive to any possible eccentricity of the opposite ends of the pair of arms. Thus the adjuster 15, which is preferably assembled into the case by nondestructive pressing of the threaded portion 152 into the threaded guide defined by extensions 14, may be inserted askew, with several threads crossed, without substantially impairing its ability to uniformly and stably adjust the spacing of the arms 32. Such a mechanical feature is of importance for a structure which is to be mass produced by automated machinery. As can be seen, this embodiment is designed so that the entire structure shown in FIG. 3 may be injection-molded as a single piece. The unit is assembled by folding the fork 15 and the nipple plates 16 upward in the manner previously described. In the course of assembly the flow tube 52 (described below) is attached, and the adjuster placed into position.

Figure 4:
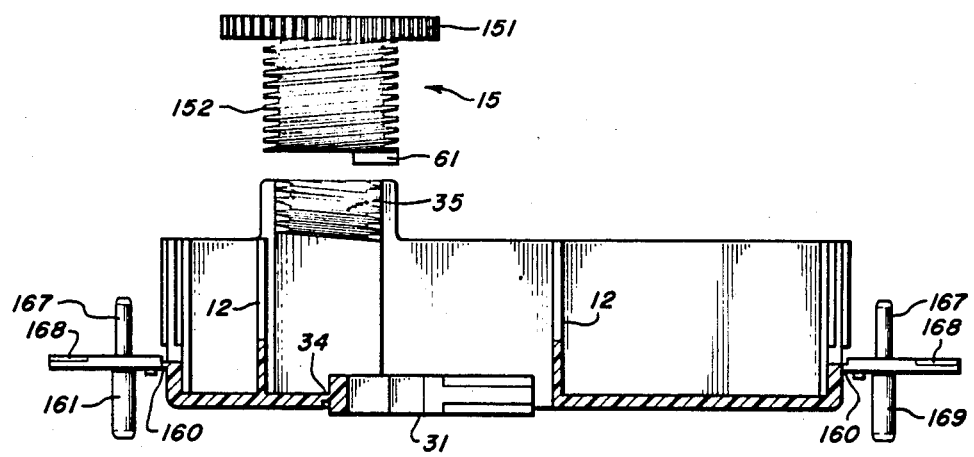
FIG. 4 is a vertical section of a side view of this embodiment before assembly, showing the adjuster in an exploded view.

FIG. 4 presents a vertical section of the embodiment of FIG. 3. In this embodiment, it may be seen that ribs 12 form a V- or U- shaped structural reinforcement for the opposing long walls of the housing. The base of the U- or V- extends below the line determined by the inner nipples 167. The inner nipples 167 at each end of the case are of a smaller size than the corresponding nipples 161, 169, for the inlet and outlet tubes, and are of a size to accommodate the flow tube which is preferably of a different composition than the conventional inlet tube 162 of FIG. 1. The fork 31 before assembly is shown lying essentially co-planar with the lower wall of the case; the hinge line 34 may be seen to be a thin, flexible portion of that wall. The guide defined by the segments of the housing extension 14 has interior threads 35 for engaging the threaded portion 152 of the adjuster 15. (Although it appears in this figure that the diameter of the bore defined by housing extension 14 is insufficient to accommodate the full diameter of the threaded adjuster portion 152, this effect is simply the result of the unusual geometry, shown more clearly in FIG. 3, of housing extensions 14.)

Figure 5:
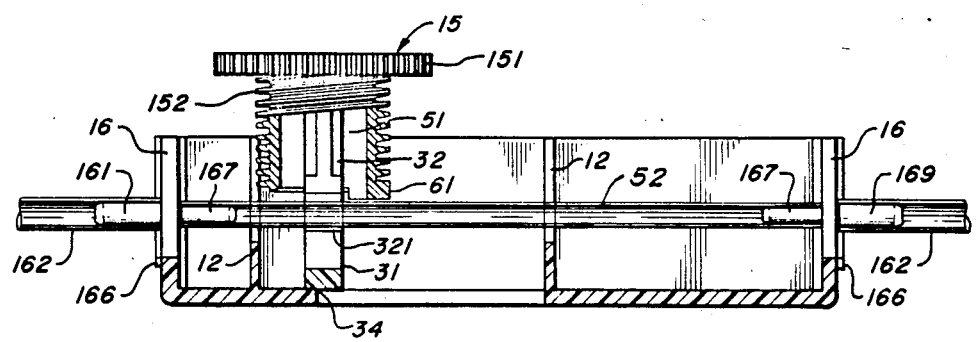
FIG. 5 is a vertical section of a side view of the clamp shown in FIG. 4, fully assembled.

Turning now to FIG. 5, there is shown another vertical section of the device of FIG. 4 in a fully assembled position. Fork 31 is rotated up and vertically centered within adjuster 15. Flow tube 52 connects the two inner nipples 167 and passes between opposing arms 32 of the fork. The flow tube 52 is a separate short length of tubing of a special composition chosen for its responsiveness and resilience, so that deformations of the tube caused by the clamp element are immediately and directly effected without cold flow or subsequent perturbations; and further having the property that the tube upon unclamping, resumes its former shape. It is formed of a compound such as that sold under the trade name Selastic (a silicone rubber compound) approved for medical use. Also shown in FIG. 5 is a unthreaded protrusion 61 of the adjuster 15. This protrusion 61 is at the extreme end of the threaded portion 152 of the adjuster, below the threads 35 of the wall extensions 14, and serves to prevent unscrewing of the adjuster beyond the point at which the adjuster initially contacts the fork. Thus when one attempts to unscrew the adjuster beyond a limit of its effective operating range, portion 152 simply jams in the threads, effectively warning the operator of this condition, and preventing further unscrewing of the adjuster.

Figure 6:
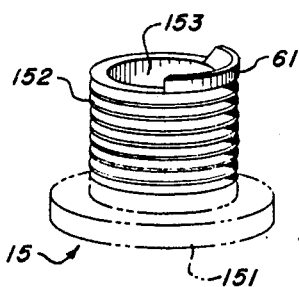
FIG. 6 shows detail of the adjuster of this embodiment.

FIG. 6 shows a detailed view of the adjuster 15, in which the gear 151 is shown schematically without teeth. As may be seen, the externally threaded portion 152 is of substantially uniform diameter extending from the gear at one end to the protrusion 61 at the other end. The protrusion 61 comprises a partial segment of the cylinder which is unthreaded and therefore extends slightly beyond the inner diameter of the threaded bore formed by threaded guides 14. The interior of the adjuster is a hollow bore 153, which in the embodiment shown is a right cylindrical bore. In use, as the adjuster advances into the case, the leading edge of this bore engages progressively lower portions on the external face of the arms 32 of the fork. The contact portions of the arms 322 taper outwardly, thus forcing the fork arms 32 closer together and causing the clamping motion. As noted above, as an alternative to this embodiment, the bore may be tapered and the arms straight, so as to achieve a substantially similar effect.

Figure 7:
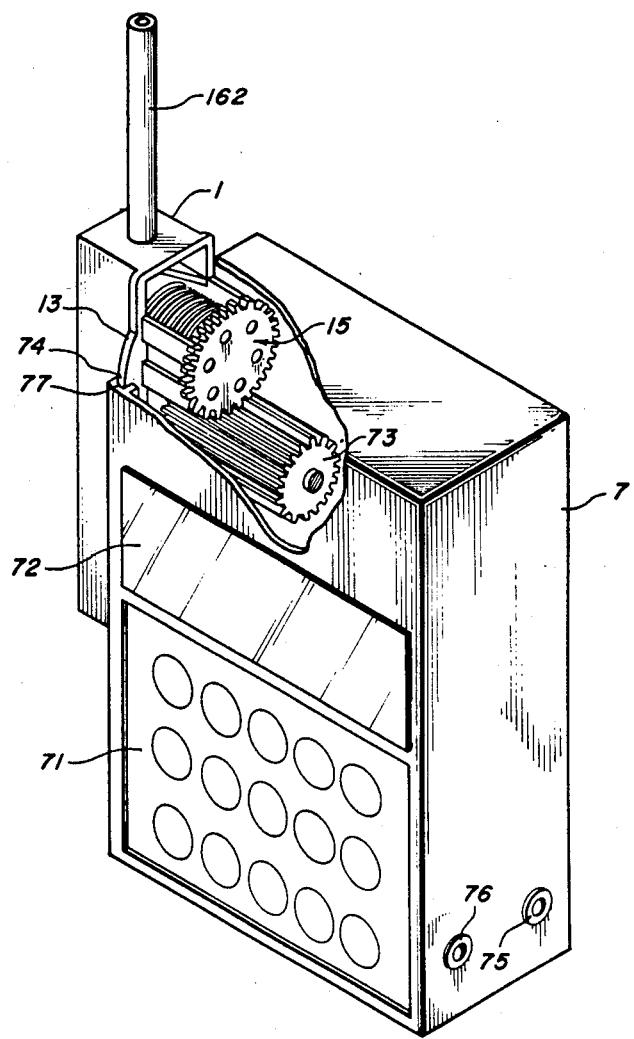
FIG. 7 shows a modular clamp system according to the present invention with a mating controller.

Turning now to FIG. 7, there is shown a modular system according to the present invention in which an automated controller 7 is adapted to receive the clamp. Controller 7 has a keyboard 71 for programming an infusion schedule, and a program display 72 which may be of the liquid crystal type, and which may, in a manner known in the art, be used for displaying program mode and giving the operator instructions or warnings related to the entry of information or the status of the medication program being run. The controller 7 is configured to accommodate the clamp in such a way that a controller drive member engages the adjuster gear 151 to rotate the adjuster in accordance with control signals generated by the program instruction. In the embodiment shown, this is accomplished by the use of a pair of parallel mounting rails 74 along one side of the controller 7 and protruding therefrom so as to form a channel 77 in the controller housing. The mounting flanges 13 of the clamp case slide into such channels, thus holding the gear of the adjuster 151 in engagement with the controller drive member 73. A drip sensor, which may be of conventional type, for sensing the rate of flow of drops in a drip chamber is attached to the controller 7 at input jack 75 and provides signals to the controller indicative of the actual rate of flow. Based upon the information from the drip sensor, and in accordance with the program data entered via keyboard 71, drive control signals cause the controller drive member 73 to adjust the clamp to increase or decrease flow in accordance with the program requirements in relation to the measured rate and cumulative dose. An auxiliary jack 76 is also provided in the controller.

In one embodiment of the control mechanism, the auxiliary jack 76 is configured to receive the input from a second drip sensor. In a hospital setting, it is often necessary to interupt the delivery of a large reservoir of infusate in order to effect the delivery of a smaller volume of a particular medicine. This is generally accomplished by manually attaching a reservoir of the specific medicine to the infusion tube and closing a valve to the large-volumed reservoir until the medicine is delivered. In one embodiment of the clamp system according to the present invention, this "piggy back" operation is performed automatically by having the controller programmed to recognize the existence of a second drip sensor input at auxiliary jack 76 and turn the adjuster 15 so as to reduce flow or close the clamp as long as auxiliary jack 76 is receiving signals indicative that the secondary drip chamber to which the auxiliary drip sensor is attached continues to have medicine flowing. When drips are no longer sensed at the auxiliary input 76 the controller reopens the major clamp and continues to operate based on the information provided at drip sensor input jack 75. The controller 7 operates with a microprocessor, which has a time base allowing it to keep track of actual elapsed time, as well as drip counters which register the total delivered volume. Thus where the actual doses and times of medicine delivered through inlet 162 to the patient are critical, the medication program of controller 7 may be set up to adjust the delivery rate so as to achieve the projected delivery schedule despite the reduction or interruption caused by the piggy back medication. It may be desirable to dispense with drip sensor input jack 75 and have the primary drip detector permanently wired to the controller so that medical personnel do not accidentally interchange the two drip sensors resulting in excessive delivery of the wrong medication. Alternatively, jacks 75 and 76 may be adapted to receive connections from distinct models of drip detector, or may included logic circuitry which in conjunction with mating circuitry of the drip detector automatically signals to the controller whether the input is a primary or secondary medication source indicating detector.

It will be appreciated that the foregoing invention has been described with reference to a particular embodiment thereof and that the details are by way of illustration and not of limitation. Numerous variations and substitutions within the scope of the invention will be apparent to those skilled in the art, and accordingly are intended to be covered by the following claims.

I claim:

1. A flow control system comprising:

a case having an inlet and an outlet port;

a tube, of which at least a portion is located within the case, connecting the inlet to the outlet port;

a pair of spaced apart arms movable with respect to each other having a central longitudinal axis and fixed to the case, and so disposd that the tube passes therebetween proximate to a tube-contact face of each arm, each arm further having at an end thereof an adjustment-contact face; and adjustment means, movably mounted with respect to the pair of arms for controlled movement along the longitudinal axis, for causing adjustable compression of adjustment-contact faces of both arms so as to move them toward one another and thereby compress the tube.

2. A flow control system according to claim 1, wherein the adjustment means includes a threaded cylindrical member, with a central bore forming an interior surface for bearing against the contact faces of the arms, the axis of the bore being generally coincident with the longitudinal axis.

3. A flow control system according to claim 2, wherein at least one of the interior surface and the adjustment contact faces is tapered.

4. A flow control system according to claim 3, wherein the cylindrical member is externally threaded and is movable mounted by engagement with a mating internally threaded adjuster guide affixed to the case.

5. A flow control system according to claim 4, wherein the adjustment means includes coupling means for engaging with a movable drive member of a drive unit for moving the adjustment means, and wherein the case includes a mounting structure to removably mount the system to the drive unit in such manner as to dispose the coupling means and the drive member in engagement with one another.

6. A flow control system according to claim 5, wherein the coupling means and the drive member are mating gears.

7. A flow control system according to claim 6, wherein the case includes a plurality of coplanar flanges and the drive unit has a plurality of parallel channels, so that by sliding the flanges along the channels, the case is removably mounted to the drive unit and the gear of the adjustment means is engaged with the drive unit gear.

8. A flow control system according to claim 4 wherein the case includes opposing side walls on either side of the pair of arms and the adjuster guide includes arcuate internally threaded extensions of the opposing sides walls.

9. A flow control system according to claim 8, wherein the case further includes at least one integrally formed rib element to maintain the opposing side walls in a dimensionally stable spaced relationship.

10. A flow control system according to claim 9, wherein the adjustment means further includes means for jamming, so as to provide a limit stop, when the threaded cylindrical member is rotated to an extreme position.

11. A flow control system according to claim 10, wherein the adjustment means includes coupling means for engaging with a movable drive member of a drive unit for moving the adjustment means, and wherein the case includes a mounting structure is removably mount the system to the drive unit in such manner as to dispose the coupling means and the drive member in engagement with one another.

12. A flow control system according to claim 11, wherein the coupling means and the drive member are mating gears.

13. A flow control system according to claim 4, wherein the adjustment means further includes means for jamming, so as to provide a limit stop, when the threaded cylindrical member is rotated to an extreme position.

14. A flow control system according to claim 3, wherein the cylindrical member is internally threaded and is movably mounted by engagement with a mating externally threaded portion of the arms, such portion including the adjustment-contact faces.

15. A flow control system according to claim 1, wherein the adjustment means includes coupling means for engaging with a movable drive member of a drive unit for moving the adjustment means, and wherein the case includes a mounting structure to removably mount the system to the drive unit in such manner as to dispose the coupling means and the drive member in engagement with one another.

16. A flow control system according to claim 15, wherein the coupling means and the drive emmber are mating gears.

17. A flow control system according to claim 16, wherein the case includes a plurality of coplanar flanges and the drive unit has a plurality of parallel channels, so that by sliding the flanges along the channels, the case is removably mounted to the drive unit and the gear of the adjustment means is engaged with the drive unit gear.

18. A flow control system according to claim 1, wherein the tube is cemented to the tube-contact faces of the arms, so that upon narrowing or widening of the space between the arms in the region between the tube contact faces, the tube is positively compressed or extended, respectively.

19. A flow control system according to claim 18, wherein the adjustment means includes coupling means for engaging with a movable drive member of a drive unit for moving the adjustment means, and wherein the case includes a mounting structure to removably mount the system to the drive unit in such manner as to dispose the coupling means and the drive member in engagement with one another.

20. A flow control system according to claim 19, wherein the coupling means and the drive member are mating gears.

21. A flow control system according to claim 20, wherein the case includes a plurality of coplanar flanges and the drive unit has a plurality of parallel channels, so that by sliding the flanges along the channels, the case is removably mounted to the drive unit and the gear of the adjustment means is engaged with the drive unit gear.

22. A flow valve comprising:

a case having two space-apart end walls with integrally formed inlet and outlet nipples respectively and means for receiving a flow tube extending between the inlet and outlet nipples; and a third wall of the case, extending between the end walls and having an integrally formed tube-compressing member hingedly attached thereto, the tube-compressing member including a fork member having two parallel arms and hinged to the third wall for rotation around a first hinge axis in such a way that the fork may be rotated up to define a passage for the flow tube between its arms.

23. A flow valve according to claim 22, wherein each arm is hinged to the fork member along an arm hinge axis, each arm hinge axis being offset from and substantially perpendicular to the first hinge axis, so that the arms may be rotated toward each other to compress the tube.

24. A flow valve according to claim 23, wherein each arm has a contact face at an end thereof and the two arms have a central longitudinal axis, such valve further comprising:
adjustment means, movably mounted in contact with a contact face of each arm for controlled movement along the central longitudinal axis, for varying the lateral spacing of the arms as it moves along the central longitudinal axis.

25. A flow valve according to claim 24, wherein the adjustment means includes an externally threaded cylinder having a central bore for receiving an end of the arms, and wherein the case includes opposing side wall members defining an internaly threaded guide for receiving the threaded cylinder, the guide being symmetrically disposed with respect to the arms when the fork has been rotated up to define a passage for the flow tube between its arms, and wherein at least one of the bore or the contact faces are tapered for varying the lateral spacing.

26. A flow valve comprising:
a case, having two spaced apart end walls integrally formed therein, with integrally formed inlet and outlet nipples, respectively, and means for receiving a flow tube extending between the inlet and outlet nipples;
a tube compressing member mounted on the case for adjustable compression of the tube;
each such end wall retaining a nipple plate containing one of the respective inlet or outlet nipples and being hingedly attached to the case and integrally formed therewith.

27. A flow valve according to claim 26, wherein the tube-compressing member comprises a pair of parallel arms hinged to the case and mounted for passage of the tube therebetween, and adjustment means for adjusting the spacing of the arms to adjustably compress such tube.

28. A flow valve according to claim 27, wherein the arms have a longitudinal axis and the adjustment means is movably mounted with respect to the pair of arms for controlled movement along the longitudinal axis.

29. A flow valve comprising:
a case, having two spaced apart end walls integrally formed therein, with inlet and outlet nipples, respectively, and means for receiving a flow tube extending between the inlet and outlet nipples;
a tube compressing member mounted on the case for adjustable compression of the tube;
each such end wall retaining a nipple plate containing one of the respective inlet or outlet nipples and being hingedly attached to the case and integrally formed therewith, each end wall further including an aperture for accommodating the nipple plate, the aperture having a lateraLly oriented groove around a portion of its periphery;
and each nipple plate further including a laterally extending wing for mating with the groove;
so that the nipple plate may be rotated around its hinge into the aperture and held thereat by a snap-fit mating of the groove and wing.

30. A flow valve according to claim 29, wherein each end wall includes a raised border portion adjacent the aperture and above the hinge, said border thereby defining the groove, and wherein the nipple plate includes a raised and laterally extending dog below the border portion, the dog being operative in the snap-fit condition to prevent the nipple plate from sliding along the groove away from the hinge.

31. A flow valve according to claim 30, wherein the tube-compressing member comprises a pair of parallel arms hinged to the case and mounted for passage of the tube therebetween, and adjustment means for adjusting the spacing of the arms to adjustably compress such tube.

32. A flow valve according to claim 31, wherein the arms have a longitudinal axis and the adjustment means is movably mounted with respect to the pair of arms for controlled movement along the longitudinal axis.

* * * * *